United States Patent [19]
Papa et al.

[11] Patent Number: 5,618,973
[45] Date of Patent: Apr. 8, 1997

[54] ESTERIFICATION PROCESS

[75] Inventors: Anthony J. Papa, St. Albans; Brian T. Keen, Charleston, both of W. Va.

[73] Assignee: Union Carbide Chemicals & Plastics Technology Corporation, Danbury, Conn.

[21] Appl. No.: 337,101

[22] Filed: Nov. 10, 1994

[51] Int. Cl.$^6$ .................................................. C07C 67/08
[52] U.S. Cl. ............................................................ 560/263
[58] Field of Search ............................................. 560/263

[56] References Cited

U.S. PATENT DOCUMENTS

| | | | |
|---|---|---|---|
| 3,404,175 | 10/1968 | Mericer | 260/488 |
| 3,692,822 | 9/1972 | Hay et al. | 260/475 R |
| 3,700,726 | 10/1972 | Johnson et al. | 260/491 |
| 4,544,453 | 10/1985 | Gupta | 203/44 |
| 4,885,383 | 12/1989 | Weber et al. | 560/103 |
| 5,101,064 | 3/1992 | Dupont et al. | 560/78 |
| 5,202,463 | 4/1993 | Ruszkay | 560/248 |
| 5,218,140 | 6/1993 | Wegman | 560/232 |
| 5,231,222 | 7/1993 | Papa et al. | 560/265 |

FOREIGN PATENT DOCUMENTS

| | | |
|---|---|---|
| 454792 | 10/1974 | Australia . |
| 138788 | 4/1970 | Czechoslovakia . |
| 158499 | 10/1985 | European Pat. Off. ........ C07C 67/08 |
| 2187757 | 1/1974 | France . |
| 1919527 | 1/1975 | Germany . |
| 3235531 | 3/1984 | Germany . |
| 157745 | 6/1992 | Poland . |
| 0089389 | 11/1979 | U.S.S.R. . |
| 1342894 | 10/1987 | U.S.S.R. . |
| 1173089 | 12/1969 | United Kingdom ............ C07C 69/02 |
| 1262645 | 2/1972 | United Kingdom ............ C07C 69/14 |
| 2271772 | 4/1994 | United Kingdom . |

OTHER PUBLICATIONS

Chem. Abstracts CA 72(17):89798y 1969 (DE 1919527 German Patent).

Chem. Abstracts CA101(3):22993g 1984 (DE 3235531 German Patent).

Chem. Abstracts CA81(3):13138y 1974 (2187757 French Patent).

Chem..Abstracts CA108(25):221292x 1987 (SU 1342894 Russian Patent).

Chem..Abstracts CA114(22):220465t 1990 (Chinese Pub. Huxue Yu Zhanhe (3) 138–41, 1990).

Chem. Abstracts CA 95(1):6533j 1979 (RO-0089389 Romanian Patent).

"Effect of Catalysts on the Esterification of Stearic Acid" by V. Peterka in *Prumysl Potravin*, vol. 27, No. 2, pp. 115–116, (1976) (English Translation).

"Studies on the Rate of Oleic Acid Esterification with Methanol" by A. Cybulski in *Chemica Stosowana*, vol. 26, No. 1, pp. 85–97, (1982), Institute of Chem. Warsaw (English Translation).

Chem. Abstracts 119 (21):225587x 1992 (157745B1 Polish Patent).

Zesz. Nauk. –Wyzsza Szk. Pedagog. im. Powstancow Slask. Opolu, [Ser]: Chem. vol. 4, Bekierz et al., "Study of the Preparation of 2–Butoxyethyl acetate . . . azeotropic agent", 1981, pp. 69–74, abstract.

*Primary Examiner*—Porfirio Nazario-Gonzalez
*Assistant Examiner*—Rosalynd A. Williams
*Attorney, Agent, or Firm*—N. L. Balmer

[57] ABSTRACT

An esterification process for producing glycol ether esters which comprises reacting a lower hydrocarbyl carboxylic acid with a glycol ether alcohol in the presence of a long chain alkyl substituted aryl sulfonic acid esterification catalyst, the alkyl radical having from 8 to 20 carbon atoms.

20 Claims, No Drawings

ESTERIFICATION PROCESS

FIELD OF THE INVENTION

This invention relates to a process for preparing glycol ether esters which comprises esterifying a glycol ether alcohol with a lower hydrocarbyl carboxylic acid in the presence of a long chain alkyl substituted aryl sulfonic acid catalyst.

BACKGROUND OF THE INVENTION

Methods for producing glycol ether esters via esterification of glycol ether alcohols are well known in the art.

For instance, lower boiling glycol ether esters such as those containing alkoxy groups of one or two carbon atoms, e.g. 1-methoxy- 2-propyl acetate and 2-ethoxyethyl acetate can be readily prepared by reacting the corresponding glycol ether alcohol with carboxylic acid in the presence of an acid catalyst. However, such types of acid catalyzed direct esterifications are generally complicated by numerous side reactions that produce significant amounts of undesirable by-products, thereby minimizing the conversion efficiency of the esterification process to its desired product ester. Lower reaction rates that might produce lower amounts of such by-products is obviously not a perfect solution to the problem, nor are complicated purification type separation techniques as disclosed e.g., in U.S. Pat. Nos. 4,544,453 and 5,202,463. Moreover, increasing the employable amount of acid catalyst (e.g. sulfuric acid) in order to increase the rate of reaction serves only to increase the amount of such by-product impurities. Such an increase in undesired by-products above the limit of tolerable acceptable amounts can significantly discolor the desired ester product and cause an early shut down of the esterification unit due to the concentration build-up of such by-products that may make their way back to the reactor via recycle. Thus, heretofore producers of such product esters have had to compromise and carry out the esterification process at whatever reaction rate coincides with the production of a tolerable acceptable amount of by-products when employing such conventional acid catalysts.

On the other hand, higher boiling glycol ether esters such as those containing alkoxy groups of three or four carbon atoms, e.g. 2-butoxyethyl acetate or diethylene glycol monobutyl ether acetate, are not readily commercially preparable via such a direct acid catalyzed esterification process. Such is due to the fact that such heretofore known acid esterification catalysts as sulfuric acid and p-toluene sulfonic acid are not stable for prolonged reaction periods at the high temperatures that are generally required to satisfactorily produce such higher boiling product esters. Such conventional acid catalysts break down and decompose after only a short period of time at such high reaction temperatures. Consequently, such higher boiling product esters are only commercially readily preparable via transesterification, as oppose to direct esterification described above. However, such transesterification processes are notoriously slow, complicated and expensive processes that require the use of an extra-value chemical to supply the ester group of the desired ester product, as disclosed e.g., in U.S. Pat. No. 3,700,726.

U.S. Pat. No. 5,231,222 is directed to the use of long chain alkyl benzene sulfonic acid catalysts to esterify alkyl alcohols with carboxylic acid to produce product esters. However, said patent is silent with regard to producing glycol ether esters which are water-soluble products derived from glycol ether alcohols and which are entirely different from the water-insoluble product esters obtained from alkyl alcohols.

SUMMARY OF THE INVENTION

It has now been discovered that such above difficulties of heretofore conventional direct esterification can be greatly minimized and the process enhanced by employing a long chain alkyl substituted aryl sulfonic acid as the esterification catalyst. Indeed it has been further discovered that even the higher boiling glycol ether esters mentioned above can be readily prepared via direct esterification in the presence of a long chain alkyl aryl sulfonic acid catalyst.

Thus it is an object of this invention to provide a direct esterification process for producing glycol ether esters in the presence of a long chain alkyl substituted aryl sulfonic acid as the esterification catalyst. Other objects and advantages of this invention will become readily apparent from the following written description and appended claims.

Accordingly, a genetic aspect of this invention can be described as an esterification process for producing a glycol ether ester having the formula

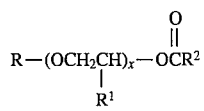

wherein R represents an alkyl radical having from 1 to 6 carbon atoms; wherein $R^1$ represents a radical selected from the groups consisting of hydrogen, methyl and ethyl radicals; wherein $R^2$ represents an alkyl radical having from 1 to 7 carbon atoms and wherein x is an integer of from 1 to 5; said process comprising reacting a glycol ether alcohol having the formula

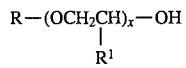

wherein R,$R^1$ and x are the same as defined above, with a lower hydrocarbonyl carboxylic acid having the formula

wherein $R^2$ is the same as defined above, in the presence of a long chain alkyl substituted aryl sulfonic acid catalyst wherein said alkyl substituent is an alkyl radical having from 8 to 20 carbon atoms, and separating and recovering the desired glycol ether ester product from water generated by said esterification.

DESCRIPTION OF PREFERRED EMBODIMENTS

As in the case with past conventional direct glycol ether ester synthesis, the process of the subject invention consists essentially of an esterification reaction wherein the glycol ether alcohol and carboxylic acid are fed to a reactor and converted in the presence of a long chain alkyl substituted aryl sulfonic acid catalyst into the desired glycol ether ester and water generated by the reaction. The volatilized product effluent containing the desired glycol ether ester, water, unreacted starting materials and in situ produced by-products is removed from the reactor and fractionally distilled. Water is removed overhead from the distillation column with the aid of an azeotroping agent, along with undesired light by-products. The unreacted glycol ether alcohol and carboxylic acid are removed as a side stream from the column, and the desired glycol ether ester product along with undesired heavy by-products is recovered from the bottom of the column.

Product glycol ether esters of this invention are those of the formula

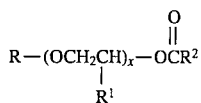

wherein R represents an alkyl radical having from 1 to 6 carbon atoms; wherein $R^1$ represents a radical selected from the group consisting of hydrogen, methyl and ethyl radicals; wherein $R^2$ represents an alkyl radical having from 1 to 7 carbon atoms; and wherein x is an integer from 1 to 5. Preferably R represents a methyl, ethyl or butyl radical, $R^1$ represents hydrogen or a methyl radical, and $R^2$ represents a methyl or ethyl radical, while x is an integer of 1 or 2. Illustrative product glycol ether esters include, e.g., 1-methoxy-2-propyl acetate (e.g., Methyl PROPASOL® Acetate, a product of Union Carbide Corporation); 2-ethoxyethyl acetate (e.g., CELLOSOLVE® Acetate, a product of Union Carbide Corporation); 2-methoxyethyl acetate (e.g., Methyl CELLOSOLVE® Acetate, a product of Union Carbide Corporation); 2-butoxyethyl acetate (e.g., Butyl CELLOSOLVE® Acetate, a product of Union Carbide Corporation); 2-hexyloxyethyl acetate: 2-(2-butoxyethoxy) ethyl acetate (e.g., Butyl CARBITOL® Acetate, a product of Union Carbide Corporation); 2-(2-hexyloxyethoxy) ethyl acetate, and the like.

Thus the carboxylic acid starting materials employable in this invention are those of the formula

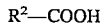

wherein $R^2$ represents an alkyl radical having from 1 to 7 carbon atoms. Such carboxylic acids as well as methods for their preparation are well known. Illustrative carboxylic acids include acetic acid, propionic acid, n-butyric acid, isobutyric acid, 2-methyl butyric acid, n-valeric acid, n-caproic acid, and 2-ethyl hexanoic acid. The preferred carboxylic acid starting materials are acetic and propionic acid, especially acetic acid. Most preferably the carboxylic acid starting materials are purified single carboxylic acids, although mixtures of such acids could be employed if desired.

The glycol ether alcohol starting materials employable in this invention are those of the formula

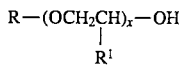

wherein R,$R^1$ and x are the same as defined above, including the preferred embodiments thereof. Such alcohols as well as methods for their preparation are well known. Illustrative glycol ether alcohol starting materials include e.g., 1-methoxy-2-propanol (e.g., Methyl PROPASOL® a product of Union Carbide Corporation); 2-ethoxyethanol (e.g., CELLOSOLVE®, a product of Union Carbide Corporation); 2-methoxyethanol (e.g., Methyl CELLOSOLVE®, a product of Union Carbide Corporation); 2-butoxyethanol (e.g., Butyl CELLOSOLVE®, a product of Union Carbide Corporation); 2-hexyloxyethanol (e.g., Hexyl CELLOSOLVE®, a product of Union Carbide Corporation); 2-(2-butoxyethoxy) ethanol (e.g., Butyl CARBITOL®, a product of Union Carbide Corporation); 2-(2-hexyloxyethoxy) ethanol (e.g., Hexyl CARBITOL®, a product of Union Carbide Corporation), and the like. Of course it is to be understood that while it may be preferred to employ glycol ether alcohol materials that are purified single alcohols, commercial products of same which are also employable herein may contain minor amounts of isomer alcohols e.g., Methyl PROPASOL® may contain some 2-methoxy-1-propanol.

Esterification catalysts employable in this invention are long chain alkyl substituted aryl sulfonic acids wherein said alkyl substituent is an alkyl radical having from 8 to 20 carbon atoms. The aryl radicals of such acids include benzene and naphthalene, the preferred aryl radical being benzene. More preferably, such esterification catalysts are long chain alkyl benzene sulfonic acids of the formula

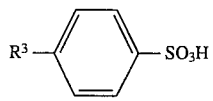

wherein $R^3$ represents an alkyl radical having from 8 to 20 carbon atoms. Such acids as well as methods form their preparation are well known. Of course it is to be understood that in addition to employing such individual acids per se, it may be more convenient or desirable to employ the commercial or technical grade compounds of such acids (i.e. a mixture of such individual acids, e.g., wherein the alkyl radical shown as $R^3$ in the above formula is commonly expressed as representing an average number of carbon atoms in the range of from 8 to 20, e.g. those normally used in manufacturing detergents). Thus, as employed herein, the above acid catalyst formula is to be considered as encompassing mixtures of the individual acid compounds represented by said formula, as well as the individual acid compounds themselves. Illustrative alkyl substituted aryl sulfonic acids, include nonyl substituted napthalene sulfonic acid, dodecyl substituted benzene ether sulfonic acid, n-octylbenzene sulfonic acid, n-undecylbenzene sulfonic acid, n-dodecylbenzene sulfonic acid, n-tridecylbenzene sulfonic acid, n-dodecylbenzene sulfonic acid, n-tridecylbenzene sulfonic acid, n-tetradecylbenzene sulfonic acid, n-pentadecylbenzene sulfonic acid, n-hexadecyl benzene sulfonic acid, n-heptadecylbenzene sulfonic acid, n-octadecylbenzene sulfonic acid, n-nonyldecyl benzene sulfonic acid, n-eicosylbenzene sulfonic acid, and mixtures thereof. Illustrative commercial grade mixtures of the alkyl benzene sulfonic acids of the above formula available to the public include Bio-Soft ® S-100 which has an equivalent weight of about 318 and wherein $R^3$ represents an average alkyl chain length of about 11.5 carbon atoms (Stepan Co.), AAS-98S a linear alkylbenzene sulfonic acid with an average alkyl chain length of $C_{11}$–$C_{12}$ (Continental Chemical Co.), Vista SA697 and Vista SA 597 a $C_{13}$ linear alkyl benzene sulfonic acid (average mol. wt. 342) and a $C_{11}$ linear alkylbenzene sulfonic acid (average mol wt. 318), respectively, (both products of the Vista Chemical Co.), Stepantan ®H-100 a branched dodecylbenzene sulfonic acid (Stepan Co.), a linear alkyl benzene sulfonic acid wherein the alkyl radical ($R^3$) constitutes about 1% $C_{10}$, 40% $C_{11}$, 28% $C_{12}$ and 31% $C_{13}$+ (Alfa Products Co.), and the like. Other illustrative catalysts are Nacure® 155, a product of King Industries which is an alkyl substituted naphthalene sulfonic add ($C_{28}H_{42}O_6S_2$; average mol. wt. 534.8) having the formula

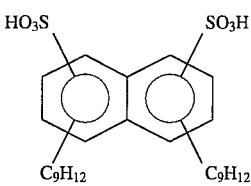

Poly-Tergent® 2A1 Acid, a product of Olin Corporation which is an alkyl substituted benzene ether sulfonic acid ($C_{36}H_{58}O_7S_2$; average mol. wt. 700) having the formula

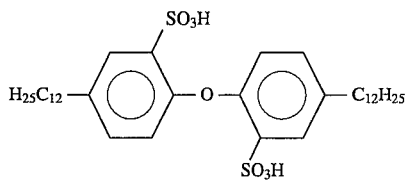

The more preferred catalysts are alkylbenzene sulfonic acids of the above formula wherein $R^3$ represents an alkyl radical having from 10 to 14 carbon atoms, the most preferred catalyst being the commercial Bio-Soft® S-100 described above (which is also referred to herein as "DBSA").

While the process of the present invention may be performed batchwise, semi-continuously, or continuously, it is preferably carried out in a continuous fashion wherein unreacted starting materials are recycled to the reactor and make up glycol ether alcohol and carboxylic acid are added to maintain a constant reaction composition.

The esterification process of this invention is a well known mildly exothermic equilibrium reaction. The basic process can be carried out in a conventional esters kettle reactor wherein volatilized product ester and water are removed from the reactor and transferred to a conventional esters distillation column for separation. Any suitable conventional esters type reactor and distillation (refining) column can be employed herein. However in view of possible acid corrosion problems over time it is preferred to employ corrosion resistant type materials, e.g., stainless steel, for the construction of such units. Moreover, it is further preferred that the ester distillation column consist of at least 30 Oldershaw trays or plates the total number of said trays or plates being constrained only by practical considerations.

The generic reaction conditions and processing techniques of this invention are generally not narrowly critical, and may correspond, if desired and appropriate to conditions heretofore employed in conventional esterification processes. Indeed, such reaction conditions and processing techniques may be varied widely and tailored to meet individual needs and produce the particular product ester desired.

Thus, the esterification process may be started by adding glycol ether alcohol and carboxylic acid to the reactor, along with some product ester and water if desired, followed by addition of the esterification catalyst. For example, an illustrative initial charge might be derived from a composition consisting of 690 grams (5.22 moles) of Methyl PROPASOL® Acetate, 200 grams (2.22 moles) Methyl PROPASOL®, 100 grams (1.67 moles) acetic acid and 10 grams (0.56 moles) water. The addition of water to the reaction composition is not essential to the process of the subject invention. The reaction contents may then be heated and the distillation (refining) brought to total reflux. Upon reaching total reflux in the distillation column an azeotroping agent, e.g., cyclohexane may be added to the top reflux of said column to aid in removing water overhead along with any lights, i.e., in situ produced by-products that boil below that of the desired glycol ether ester product. In this manner unreacted glycol ether alcohol and carboxylic acid may be removed as a side stream from the distillation column and recycled to the reactor, while the desired glycol ether ester product, and any heavies, i.e., in situ produced by-products that boil above that of said product ester, is recovered from the bottom of the distillation column. The reaction system can be lined out to constant conditions within about 24 hours to achieve steady-state reaction composition.

After equilibrium has been achieved the glycol ether alcohol and carboxylic acid are fed continuously to the reactor, preferably in a substantially equimolar ratio. As employed herein the expression substantially equimolar ratio includes molar ratios of alcohol to acid in the range of from about 1 to 1.5:1. Of course such includes equimolar ratios of such reactants and higher or lower glycol ether to carboxylic acid ratios may also be employed if desired. In general it is preferred to employ a slight excess of alcohol to the acid (e.g., about a 1.05:1 molar ratio of alcohol to acid).

The quantity of esterification catalyst employed in this invention can be any catalytic amount that will advance the reaction rate of the process. However, preferably the catalyst should obviously produce a rapid reaction. Thus the concentration of the alkyl substituted aryl (preferably benzene) sulfonic acid esterification catalysts of this invention in the esters batch still reactor may be in the range of about 0.01 to about 5.0 wt. % acidity, calculated as wt. % $H_2SO_4$. Preferably it is maintained in the range of from about 0.1 to about 2.0 wt. % and more preferably from about 0.2 to about 0.8 wt. % calculated as wt. % $H_2SO_4$. The catalyst level should preferably remain constant and may be monitored by titration. For instance, it is to be understood that the initial charge of catalyst will itself be esterified as the reaction proceeds and eventually line out at a slightly lower constant free acid value where equilibrium between the catalyst and glycol ether alcohol is achieved, unlike sulfuric acid which never lines out. If the acidity level should drop below an acceptable level, makeup catalyst may be added to the reactor to achieve whatever reaction rate is desired.

The esterification process of this invention may be operated at any suitable reaction temperature and pressure. For instance, the generic process described herein may be operated at pressures ranging from about 5 mm Hg. (0.13 kPa) to about 1300 mm Hg. (173.32 kPa), preferred pressures ranging from about 100 mm Hg. (13.33 kPa) to about 1034 mm Hg. (137.86 kPa). Likewise, the esterification reaction may be generically conducted at a temperature ranging from about 80° C. to about 225° C. and preferably from about 100° C. to about 205° C. Of course the most preferred reaction conditions in any one individual circumstance will depend to a large extent upon the particular product ester and processing efficiency desired by the operator and such conditions may be readily determinable by one skilled in the art following the more preferred aspects of this invention as explained herein and/or through simple routine experimentation. For example, it has been found that lower boiling glycol ether esters such as 1-methoxy-2-propyl acetate and 2-ethoxyethyl acetate can be readily obtained by maintaining processing pressure at a pressure ranging from about atmospheric (760 mm Hg. or 101 kPa) to slightly above atmospheric, e.g., about 827.44 mm Hg. (110.32 kPa) to about 1034.30 mm Hg. ( 137.90 kPa) and at a reactor temperature of about 120° C. to about 145° C. On the other hand, higher boiling glycol ether esters may be preferably obtained by maintaining the processing pressure at a pressure ranging from about 50 mm Hg. (6.67 kPa) to about atmospheric (760 mm Hg. or 101.32 kPa) and at a reactor temperature in the range of about 150° C. to about 205° C. For example, 2-butyloxyethoxy acetate may be preferably obtained by maintaining the processing pressure at about atmospheric pressure (760 mm Hg. or 101.32 kPa) and at a reactor temperature in the range of about 170° C. to about 190° C., more preferably at about 180° C. However, no volatilized 2-(2-butoxyethoxy)ethyl acetate product was obtained at 180° C. to 220° C. at atmospheric pressure with Bio Soft® S-100 catalyst. Instead a reduced processing pressure of from about 50 mm Hg. to about 300 mm Hg., is recommended to volatilize the 2-( 2-butoxyethoxy)ethyl acetate at a reactor temperature of about 150° C. to about 205° C. The more preferred reduced processing pressure for said acetate being in the range of from about 160 mm Hg. (21.33 kPa) to about 200 mm Hg. (26.66 kPa) and the preferred reactor temperature being from about 170° C. to about 190° C., more preferably about 180° C. Of course it is desirable not to force too high a reaction temperature in order to maintain low amounts of by-product impurities and high product ester purifies. Most preferably the esterification process of this invention is carried out at steady-state operating conditions so as to promote as much consumption of the alcohol as possible.

The subject esterification process of this invention involves a substantially anhydrous reaction medium, i.e. one containing no more than about 1–2 wt. % water, in the reactor. Limiting the amount of water in the reactor to such minor amounts permits high reaction rates and assures maximum product ester concentration in the reactor. Such low concentrations of water are achievable because while the esterification process produces water as a by-product, both the product ester and water formed are readily distilled from the reactor.

The continuous esterification process of this invention preferably employs a conventional condenser wherein part or all of the vaporized crude glycol ether ester product effluent, which also contains some unreacted glycol ether alcohol and carboxylic acid, by-products and water, removed from the reactor may be condensed in any suitable manner, prior to being passed to the distillation (refining) column. For instance, lower boiling ether esters such as 1-methoxy-2-propyl acetate and 2-ethoxyethanol acetate may be condensed at 95° C. to 120° C. at atmospheric pressure (760 mm Hg. or 101 kPa), while higher boiling esters such as 2-butoxyethyl acetate may be condensed at 115° C. to 130° C. at atmospheric pressure. While condensation of the vaporized crude glycol ether ester product effluent prior to its addition to the distillation column is not absolutely necessary, it is generally preferred to condense at least part e.g., about 75 to 80% by weight said vaporized effluent. The vapor feed and temperature of the liquid feed from the condenser help control and supplement the total heat used to operate the distillation column.

The condensed crude glycol ether ester product liquid along with the remaining uncondensed crude ester product effluent are both fed to the distillation (refining) column, preferably at about or slightly above its midpoint. Any suitable heated column base that drives the vaporized unreacted glycol ether alcohol and carboxylic acid, water and light by-products up the column may be employed herein and preferred temperatures may be easily determined by routine experimentation. For example, in the case of lower boiling glycol ether esters, such as 1-methoxy-2-propyl acetate, it is preferred to maintain a base temperature of about 160° C. at 310.29 mmHg. or 41.37 kPa, while in the case of 2-butoxyethyl acetate the base temperature is preferably about 195° C. at atmospheric pressure. As noted above, unreacted alcohol and acid starting materials may be removed from the distillation column as a side stream at slightly above the point at which the liquid and vaporized ester product were added to the column and the unreacted glycol ether alcohol and carboxylic acid so collected, pumped as a liquid recycle back to the reactor.

An azeotroping agent is added to the top reflux of the distillation column to help remove the water and light by-products. Any suitable azeotroping agent may be employed such as aromatic hydrocarbons, alkanes, cycloalkanes, aliphatic ethers, esters and ketones, and the like, such as benzene, toluene, hexane, cyclohexane, di-n-propylether, etc. The preferred azeotroping agent is cyclohexane. For example, the volatilized cyclohexane-water azeotrope and light by-products are taken overhead from the distillation column, condensed and passed to a conventional aqueous azeotrope decanter wherein it is allowed to phase separate into a top layer of cyclohexane and an aqueous bottom layer containing said lights. The cyclohexane rich top layer of the decanter can be reemployed as the azeotrope by pumping it to the top reflux of the distillation compound. Fresh cyclohexane if desired can be periodically added to the cyclohexane feed line to the distillation column to replace any small amount of cyclohexane that might be lost in the vent system. Likewise, a small amount of fresh distilled water, if desired, may also be periodically added to the top reflux of the distillation column, e.g., via the cyclohexane feed line to cool the top reflux of the column and to help satisfy the cyclohexane-water azeotrope. Any suitable azeotroping conditions may be employed and such may easily be determined by routine experimentation. For example, in the case of cyclohexane it is preferred to maintain the top reflux of the distillation column at about 74° C. and 103.43 mmHg. or 13.79 kPa. The bottom water layer of the decanter separated from the cyclohexane may be discarded as aqueous waste or collected to recover any significant amount of unreacted glycol ether alcohol that may have been removed along with the light by-product impurities and the cyclohexane-water azeotrope. For instance, unreacted 2-ethoxyethanol is not found in significant amounts in the bottom water layer of the decanter, thus allowing said bottom water layer to be directly discarded as waste water. On the other hand, significant amounts of unreacted 1-methoxy-2-propanol have been found in the bottom water layer of the decanter. Such amounts of unreacted 1-methoxy-2-propanol do not environmentally allow for the collected water layer from the decanter to be directly discarded as waste water. In such cases it is preferred to first process the collected decanter bottom water layer by distillation in a separate column to remove at least some of the light by-product impurities that may also be present in such aqueous decanter tails, since increased by-product levels in the reactor can eventually cause an undesirable colored ester. The unreacted starting glycol ether alcohol (e.g., 1-methoxy-2-propanol) in the form of an aqueous azeotrope recovered from said distillation is then recycled to the reactor, The desired glycol ether ester product which may contain some small amounts of in situ produced heavy by-products is then recovered as a tails stream from the base of the distillation (refining) column.

Further, if desired, vent gas from the overhead of the decanter may be purified by passing it in a counter current fashion through a stream of the starting glycol ether alcohol in a scrubber to remove any organics and the organic rich starting glycol ether alcohol bottoms from the scrubber fed to the reactor, while the top stream from the scrubber may be fed to a second water-scrubber to remove any remaining dissolved glycol ether alcohol. If desired, the bottom water stream from said second scrubber may be fed to the reflux of the distillation column via the cyclohexane azeotrope feed line and the top stream from the second scrubber vented to the atmosphere or used as a fuel.

Beneficial factors involved in the employment of the alkyl substituted aryl sulfonic acid catalysts in the esterification process of this invention are many, not the least of which is the production of product esters with reduced by-product impurities formation as compared to that heretofore obtainable with comparable amounts of conventional acid catalysts (e.g., $H_2SO_4$), without any undue sacrifice to the desired rate of ester product production. The alkyl substituted sulfonic acids employable in this invention are highly selective and active catalysts for the production of the desired glycol ether ester products. It has also been surprisingly discovered that the long chain alkyl aryl sulfonic acid catalysts can be readily used to produce high boiling ester products via direct esterification, since the catalysts of this invention are stable and do not decompose at the high reactor temperatures necessarily employed to produce such ester products. Accordingly, the production desired ester product can be increased by using higher amounts of the catalysts of this invention above that normally obtained when employing conventional catalysts, while maintaining about the same total amount of by-product formation. Alternatively, the total amount of such by-product formation can be lessened by employing comparable amounts of the catalysts of this invention to that normally employed with conventional catalysts, while maintaining about the same catalyst activity, i.e., comparable rates of ether ester product formation. Moreover, overall quality of ester product and processing performance is enhanced because of the lower amounts of by-product formation that may be associated with the use of the catalysts of this invention, e.g., lower by-product impurities translate into a better color quality for the desired ester product, as well as lower corrosion and line fouling problems. In addition, the catalysts of this invention are biodegradable and their stability helps provide a more stable processing operation (e.g., make-up catalyst additions are not normally needed during the esterification process).

Finally the product esters of the esterification process of this invention have a wide range of utility that is well known and documented. For example, such esters are especially useful e.g. as solvents in paints and inks, as well as coalescing aids in may other coating formulations, and the like.

The following examples are illustrative of the present invention and are not to be regarded as limitive. It is to be understood that all parts, percentages and proportions referred to herein and in the appended claims are by weight unless otherwise indicated.

CATALYST CONCENTRATIONS DETERMINATIONS

The process employed by this invention in determining the alkyl aryl sulfonic acid catalyst concentration in the reaction kettle in terms of sulfuric acid involves titration with a base. This method actually determines sulfuric acid as the monobasic acid, monobutyl sulfonate, but the results are reported as percent sulfuric acid for convenience. The procedure is as follows:

1. Into each of two 250 mL glass-stoppered flasks pipet 10 mL of sample and add 8 to 10 drops of thymol blue-xylene cyanol FF indicator.
   Indicator: 3.0 grams of thymol blue (Na salt from Baxter Scientific Products) and 0.8 grams of xylene cyanol FF (from Fisher, catalog#1131069) dissolved in 1 liter of DMF.
2. Add 100 mL of neutralized anhydrous isopropanol to each of the flasks.
3. Immediately titrate the contents of each flask with standard 0.1 N morpholine in isopropanol to a color change from purple to green. Approach the end point dropwise using a 25 mL buret.
4. Calculation:
   Sulfuric Acid, % by weight=A×N×9.81/10×Sp.Gv.
   A =ML of N normal morpholine solution required for the sample.

EXAMPLE 1

An esterification process was carried out in which Methyl PROPASOL® was reacted with acetic acid in the presence of Bio-Soft ® S-100 (DBSA) as the esterification catalyst and said process compared to the same process using sulfuric acid ($H_2SO_4$) as the esterification catalyst. The amounts of catalyst employed in each instance were essentially the same, i.e., about 0.1 weight percent calculated as sulfuric acid, as were the other reaction conditions of the comparison. The results in the following table are reported in terms of average area % gas chromatographic analysis and illustrate the decrease by-product formation (i.e., impurities) that was achieved when the long chain benzene sulfonic acid catalyst of this invention was employed.

TABLE 1

| Products | $H_2SO_4$ Catalyst | | DBSA Catalyst | |
| --- | --- | --- | --- | --- |
| (Avg. Area %) | Reactor Kettle | Reactor Overhead | Reactor Kettle | Reactor Overhead |
| $H_2SO_4$, wt % | 0.106–0.082 | | | |
| DBSA (as wt % $H_2SO_4$) | | | 0.15–0.107 | |
| HOAc | 12.3 | 14.18 | 13.02 | 14.71 |
| MePs | 16.2 | 30.17 | 16.63 | 31.45 |
| MePsAc | 70.6 | 49.78 | 69.55 | 48.94 |
| $H_2O$ | 0.6 | 5.32 | 0.57 | 5.10 |
| Methanol* | 0.0 | 0.30 | 0.0 | 0.002 |
| Propion- aldehyde* | 0.010 | 0.034 | 0.008 | 0.020 |
| Methyl Acetate* | 0.013 | 0.034 | 0.0 | 0.016 |
| Allyl Alcohol* | 0.011 | 0.009 | 0.0 | 0.001 |
| PGDAC** | 0.141 | 0.016 | 0.106 | 0.001 |

HOAc = acetic acid
MePs = Methyl PROPASOL ®
MePsAc = Methyl PROPASOL ® Acetate
*Major Light By-Products
**Propylene glycol diacetate, a major heavy by-product
Conditions: Each Process involved continuously feeding Methyl PROPASOL ® and acetic acid in an equimolar (1:1) ratio to a laboratory reactor and maintaining a constant reaction composition for 25 hours at 132° C. at atmospheric pressure, overhead temperature 126–127° C., gas chromatographic analysis being conducted every two hours.

The above results show that the alkyl benzene sulfonic acid catalyst substantially reduces the formation of impurities (by-products). The data indicates that it would take about 6 times as much DBSA catalyst, i.e., Bio-Soft® S-100

(or about 0.6 weight % measured as sulfuric acid) to achieve the same impurity level in the reactor overhead as 0, weight percent sulfuric acid. This means that compared to a typical process catalyzed with 0.1 weight percent sulfuric acid, the process of the subject invention can be conducted at either the same or better rate of desired ester production while producing only about one-sixth as much impurities with 0.1 weight percent Bio-Soft® S-100 (measured as sulfuric acid), or at a substantial higher rate of desired ester production while producing only an equivalent amount of impurities with 0.6 weight percent Bio-Soft® S-100 (measured as sulfuric acid).

EXAMPLE 2

The following model studies were conducted to determine the sensitivity of CELLOSOLVE® (2-ethoxyethanol) to acid catalysis by a long chain alkyl benzene sulfonic acid, i.e., Bio-Soft® S-100, (DBSA), as compared to $H_2SO_4$ (concentrated sulfuric acid). In this study the various reaction products formed from the reaction of said glycol ether alcohol (i.e., CELLOSOLVE®) with said acids ($H_2SO_4$ vs. DBSA) were recorded at varying concentrations via gas chromatographic analysis. The results are given in TABLE 2 below.

TABLE 2

| Avg. Area % of Each Product | | | | | | |
|---|---|---|---|---|---|---|
| $H_2SO_4$, wt % | 0.245 | 0.343 | 1.37 | 1.52 | 2.40 | 4.40 |
| AcH + EtOH + EtAc | 0.01 | 0.009 | 0.088 | 0.178 | 0.278 | 0.866 |
| DiEt CELL + DiEth Et Ether | 0.01 | 0.008 | 0.038 | 0.06 | 0.13 | 0.672 |
| CELLO-SOLVE® | 99.826 | 99.842 | 99.435 | 99.023 | 99.589 | 95.498 |
| Unknown Heavies | 0.012 | 0.015 | 0.242 | 0.454 | 0.707 | 1.997 |
| DBSA (as wt % $H_2SO_4$) | 0.245 | 0.49 | 1.07 | 3.06 | 4.80 | 5.21 |
| AcH + EtOH + EtAc | 0.003 | 0.013 | 0.016 | 0.067 | 0.075 | 0.081 |
| DiEt CELL + DiEth Et Ether | 0.00 | 0.008 | 0.025 | 0.354 | 0.335 | 0.328 |
| CELLO-SOLVE® | 99.826 | 99.871 | 99.717 | 98.528 | 98.006 | 97.727 |
| Unknown Heavies | 0.011 | 0.074 | 0.055 | 0.153 | 0.163 | 1.139 |

AcH = acetaldehyde
EtOH = ethanol
EtAc = ethyl acetate
DiEt CELL = diethyl CELLOSOLVE ®
DiEth Et Ether = diethoxy diethyl ether
Procedure: The appropriate amount of catalyst was added to separate bottles containing about 50 gms of pure CELLOSOLVE ®. The bottles were shaken for two minutes and analyzed for $H_2SO_4$, and by gas chromatography after standing for 2 hours at ambient (25° C.). Standing for longer times e.g., 24 hours did not change the results.

The results show that CELLOSOLVE® formed greater amounts of esterification type by-product impurities when treated with $H_2SO_4$ as compared to DBSA catalyst (i.e., Bio-Soft® S-100) under the same reaction conditions.

EXAMPLE 3

The following laboratory studies demonstrated that Butyl CELLOSOLVE® Acetate (BuCsAc) and Butyl CARBITOL® Acetate (BuCbAc) can be readily produced by direct esterification of Butyl CELLOSOLVE® (BuCs) or Butyl CARBITOL® (BuCb) with acetic acid respectively.

The preparation of BuCsAc proceeded readily at about 180° C. at atmospheric pressure with DBSA catalyst (Bio-Soft® S-100,) calculated as $H_2SO_4$. There was no indication of loss of catalyst activity due to catalyst decomposition during the process.

The preparation of BuCbAc required reduced pressure at the reaction temperature of about 180° C to give volatilized ester product. The reaction proceeded smoothly with DBSA (calculated as $H_2S_4$) with no evidence of catalyst decomposition during the process. Volatilized ester product was not obtained at 180°–220° C. at atmospheric pressure.

The results are summarized in Table 3 below.

TABLE 3

| Products | BuCsAc (a) | | BuCbAc (a) | |
|---|---|---|---|---|
| Avg. Area % | Reactor Kettle | Reactor Overhead | Reactor Kettle | Reactor Overhead |
| DBSA (as wt. % $H_2SO_4$) | 0.30–0.18 | | 0.48–0.34 | |
| $H_2O$ | 0.18 | 6.82 | 0.15 | 2.5 |
| Acetic Acid | 2.01 | 16.10 | 1.1 | 11.0 |
| BuCs | 12.51 | 22.74 | | |
| BuCsAc | 84.17 | 53.79 | | |
| BuCb | | | 25.80 | 34.10 |
| BuCbAc | | | 68.5 | 49.70 |
| Total Lights | 0.11 | 0.27 | 1.1 | 1.3 |
| Total Heavies | 0.79 | 0.18 | 2.5 | 0.72 |
| Total By-Products | 0.90 | 0.45 | 3.6 | 2.02 |
| Kettle Temperature °C. | 177–180 | | 180–185 | |
| Overhead Temp. °C. | | 155–160 | | 128 |
| Kettle Press., (mmHg) | 760 (101 kPa) | | 160–200 (21.33–26.66 kPa) | |

(a) Data represents 42 hrs. run time in the lab reactor, wherein the starting materials were fed to the reactor in a 1:1 molar ratio of reactants, gas chromatographic analysis being conducted about every two hours.

The very low acetic acid and high BuCsAc and BuCbAc products values in the reactor indicate that reaction is very rapid. Analysis of the overhead fractions showed that BuCsAc and BuCbAc products are removed overhead at average concentrations of 54% and 50%, resp. Such is comparable to that obtained when 1-methoxy-2-propyl acetate is produced.

EXAMPLE 4

An esterification process was carried out in which Methyl PROPASOL® (MePs) was reacted with acetic acid (HOAc) in the presence of various long chain alkyl aryl sulfonic acids as the esterification catalyst to produce Methyl PROPASOL® ACETATE (MePsAc) and compared to the same process using sulfuric acid ($H_2SO_4$) as the esterification catalyst. The amounts of the long chain alkyl aryl sulfonic acid catalysts employed in each instance were greater then the amount of sulfuric acid catalyst employed. The other reaction conditions of the comparison were the same except the duration of the $H_2SO_4$ catalyzed run was about 24.5 hours while the duration of the long chain alkyl substituted aryl sulfonic acid catalyzed runs were about 26 hours. The following table illustrates the decrease in by-product formation (i.e., impurities) that was achieved when the long chain aryl sulfonic acid catalysts of this invention were employed.

TABLE 4

| Catalyst | Area % of Each Product | |
| --- | --- | --- |
| | Reactor Kettle | Reactor Overhead |
| $H_2SO_4$, wt % | 0.106–0.082 | |
| HOAc | 12.3 | 14.18 |
| MePs | 16.2 | 30.17 |
| MePsAc | 70.6 | 49.78 |
| $H_2O$ | 0.6 | 5.32 |
| Total Lights | 0.270 | 0.337 |
| Total Heavies | 0.200 | 0.019 |
| Total By-Products | 0.470 | 0.356 |
| Bio-Soft ® S-100 (as wt % $H_2SO_4$) | 0.50–0.32 | |
| HOAc | 10.54 | 12.5 |
| MePs | 13.2 | 26.9 |
| MePsAc | 75.2 | 54.1 |
| $H_2O$ | 0.5 | 6.2 |
| Total Lights | 0.155 | 0.207 |
| Total Heavies | 0.143 | 0.107 |
| Total By-Products | 0.298 | 0.314 |
| Nacure ® 155 (as wt % $H_2SO_4$) | 0.62–0.44 | |
| HOAc | 11.97 | 11.89 |
| MePs | 10.95 | 23.99 |
| MePsAc | 74.97 | 56.67 |
| $H_2O$ | 0.47 | 7.20 |
| Total Lights | 0.093 | 0.166 |
| Total Heavies | 0.200 | 0.014 |
| Total By-Products | 0.293 | 0.180 |
| Poly-Tergent ® 2Al Acid (as wt % $H_2SO_4$) | 0.62–0.50 | |
| HOAc | 9.10 | 11.40 |
| MePs | 12.09 | 25.99 |
| MePsAc | 76.35 | 54.42 |
| $H_2O$ | 0.48 | 7.90 |
| Total Lights | 0.079 | 0.193 |
| Total Heavies | 0.154 | 0.018 |
| Total By-Products | 0.233 | 0.211 |

Conditions: Each Process involved continuously feeding Methyl PROPASOL ® and acetic acid in an equimolar (1:1) ratio to a laboratory reactor and maintaining a constant reaction composition at about 132–135° C. at atmospheric pressure, overhead temperature about 122–127° C., gas chromatographic analysis being conducted every two hours.

EXAMPLE 5

An esterification process was carried out in which CELLOSOLVE® (Cs) was reacted with acetic acid (HOAc) in the presence of Bio-Soft® S-100 (DBSA) to produce CELLOSOLVE® Acetate (CsAc). The following table illustrates the reaction conditions and results obtained in terms of average area % gas chromatographic analysis.

TABLE 5

| Products Avg. Area % | Avg. Area % of Each Product | |
| --- | --- | --- |
| | Reactor Kettle | Reactor Overhead |
| DBSA (wt % $H_2SO_4$) | 0.41–0.37 | |
| $H_2O$ | 0.31 | 7.09 |
| HOAc | 4.91 | 9.40 |
| Cs | 8.12 | 17.95 |

TABLE 5-continued

| Products Avg. Area % | Avg. Area % of Each Product | |
| --- | --- | --- |
| | Reactor Kettle | Reactor Overhead |
| CsAc | 85.44 | 65.25 |
| Total Lights | 0.09 | 0.07 |
| Total Heavies | 0.29 | 0.15 |
| Total By-Products | 0.38 | 0.22 |
| Kettle Temperature °C. | 145–149 | |
| Overhead Temperature °C. | | 135–137 |
| Kettle Press., (mmHg) | 760 (101 kPa) | |

Conditions: The process involved continuously feeding CELLOSOLVE ® and acetic acid in an equimolar (1:1) ratio to a laboratory reactor and maintaining a constant reaction composition for about 22 hours, gas chromatographic analysis being conducted every two hours.

Various modifications and variations of this invention will be obvious to a worker skilled in the art and it is to be understood that such modifications and variations are within the purview of this application and the spirit and scope of the appended claims.

What is claimed is:

1. An esterification process for producing a glycol ether ester having the formula

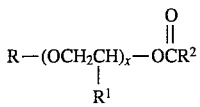

wherein R represents an alkyl radical having from 1 to 6 carbon atoms; wherein $R^1$ represents a radical selected from the groups consisting of hydrogen, methyl and ethyl radicals; wherein $R^2$ represents an alkyl radical having from 1 to 7 carbon atoms and wherein x is an integer of from 1 to 5; said process comprising reacting a glycol ether alcohol having the formula

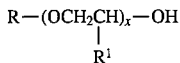

wherein R,$R^1$ and x are the same as defined above, with a lower hydrocarbonyl carboxylic acid having the formula

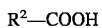

wherein $R^2$ is the same as defined above, in the presence of a long chain alkyl substituted aryl sulfonic acid catalyst wherein said alkyl substituent is an alkyl radical having from 8 to 20 carbon atoms, and separating and recovering the desired glycol ether ester product from water generated by said esterification; said recovered glycol ether ester product having reduced by-product impurities.

2. A process as defined in claim 1, wherein the esterification catalyst is an alkylbenzene sulfonic acid represented by the formula

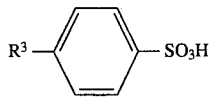

wherein $R^3$ is an alkyl radical having from 8 to 20 carbon atoms.

3. A process as defined in claim 2, wherein $R^3$ is an alkyl radical having from 10 to 14 carbon atoms.

4. A process as defined in claim 1, wherein the glycol ether alcohol is selected from the group consisting of 1-methoxy-2-propanol, 2-methoxy-1-propanol, 2-ethoxyethanol and 2-methoxyethanol and wherein the carboxylic acid is acetic acid.

5. A process as defined in claim 1, wherein the glycol ether alcohol is selected from the group consisting of 2-butoxyethanol and 2-(2-butoxyethoxy) ethanol and wherein the carboxylic acid is acetic acid.

6. A process as defined in claim 4, wherein the esterification catalyst is an alkylbenzene sulfonic acid represented by the formula

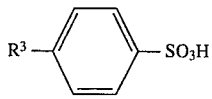

wherein $R^3$ is an alkyl radical having from 8 to 20 carbon atoms.

7. A process as defined in claim 6 wherein $R^3$ is an alkyl radical having from 10 to 14 carbon atoms.

8. A process as defined in claim 6, wherein the catalyst is a mixture of alkylbenzene sulfonic acids in which $R^3$ of the formula represents an alkyl radical having an average of about 11.5 carbon atoms.

9. A process as defined in claim 4, wherein the glycol ether alcohol is 1-methoxy-2-propanol.

10. A process as defined in claim 4, wherein the glycol ether alcohol is 2-ethoxyethanol.

11. A process as defined in claim 5, wherein the esterification catalyst is an alkylbenzene sulfonic acid represented by the formula

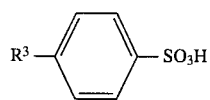

wherein $R^3$ is an alkyl radical having from 8 to 20 carbon atoms.

12. A process as defined in claim 11, wherein $R^3$ is an alkyl radical having from 10 to 14 carbon atoms.

13. A process as defined in claim 11, wherein the catalyst is a mixture of alkylbenzene sulfonic acids in which $R^3$ of the formula represents an alkyl radical having an average of about 11.5 carbon atoms.

14. A process as defined in claim 5, wherein the glycol ether alcohol is 2-butoxyethanol.

15. A process as defined in claim 5, wherein the glycol ether alcohol is 2-(2-butoxyethoxy) ethanol.

16. A process as defined in claim 8, wherein the glycol ether alcohol is 1-methoxy-2-propanol.

17. A process as defined in claim 8, wherein the glycol ether alcohol is 2-ethoxyethanol.

18. A process as defined in claim 13, wherein the glycol ether alcohol is 2-butoxyethanol.

19. A process as defined in claim 13, wherein the glycol ether alcohol is 2-(2-butoxyethoxy) ethanol.

20. A process as defined in claim 1, wherein the alkylbenzene sulfonic acid is dodecylbenzene sulfonic acid.

* * * * *